US005686088A

United States Patent [19]

Mitra et al.

[11] Patent Number: 5,686,088
[45] Date of Patent: *Nov. 11, 1997

[54] ANTIMICROBIAL WIPE COMPOSITIONS

[75] Inventors: Sekhar Mitra; George Endel Deckner, both of Cincinnati, Ohio

[73] Assignee: The Procter & Gamble Company, Cincinnati, Ohio

[*] Notice: The portion of the term of this patent subsequent to Oct. 16, 2015, has been disclaimed.

[21] Appl. No.: 589,786

[22] Filed: Jan. 22, 1996

Related U.S. Application Data

[63] Continuation of Ser. No. 173,333, Dec. 23, 1993, abandoned.

[51] Int. Cl.$^6$ .............................. A01N 25/10; A61K 9/70
[52] U.S. Cl. .................. 424/404; 424/78.07; 424/78.35; 424/78.37; 424/449; 424/422; 424/446
[58] Field of Search .......................... 424/78.07, 78.35, 424/78.37, 404, 419, 422–438, 487, 443, 445, 449

[56] References Cited

U.S. PATENT DOCUMENTS

| | | | |
|---|---|---|---|
| 3,047,445 | 7/1962 | Gresham | 154/46 |
| 3,050,217 | 8/1962 | Mackey et al. | 222/211 |
| 3,616,133 | 10/1971 | Thomas | 161/57 |
| 3,654,064 | 4/1972 | Laumann et al. | 161/156 |
| 3,666,608 | 5/1972 | Mattes | 161/62 |
| 3,674,617 | 7/1972 | Mattes | 161/62 |
| 3,709,764 | 1/1973 | Thomas | 156/177 |
| 3,717,655 | 2/1973 | Godefroi et al. | 260/309 |
| 3,726,750 | 4/1973 | Stillings | 161/57 |
| 3,881,210 | 5/1975 | Drach et al. | 15/104.93 |
| 3,965,518 | 6/1976 | Muoio | 15/104.93 |
| 3,965,519 | 6/1976 | Hermann | 15/104.93 |
| 4,075,033 | 2/1978 | Knox et al. | 134/6 |
| 4,078,071 | 3/1978 | Walker | 424/273 |
| 4,112,167 | 9/1978 | Dake et al. | 428/154 |
| 4,154,883 | 5/1979 | Elias | 428/171 |
| 4,200,097 | 4/1980 | Hobbs, Jr. et al. | 128/251 |
| 4,276,338 | 6/1981 | Ludwa et al. | 428/137 |
| 4,287,251 | 9/1981 | King et al. | 428/198 |
| 4,298,649 | 11/1981 | Meitner | 428/198 |
| 4,358,449 | 11/1982 | Heeres et al. | 424/248.58 |
| 4,408,437 | 10/1983 | Crouch et al. | 53/431 |
| 4,436,780 | 3/1984 | Hotchkiss et al. | 428/198 |
| 4,600,620 | 7/1986 | Lloyd et al. | 428/195 |
| 4,615,697 | 10/1986 | Robinson | 604/890 |
| 4,636,202 | 1/1987 | Lowin et al. | 604/236 |
| 4,675,226 | 6/1987 | Ott | 428/102 |
| 4,983,392 | 1/1991 | Robinson | 424/427 |
| 5,043,463 | 8/1991 | Carraher, Jr. et al. | 556/88 |
| 5,147,646 | 9/1992 | Graham | 424/424 |
| 5,225,196 | 7/1993 | Robinson | 424/427 |
| 5,238,843 | 8/1993 | Carpenter et al. | 435/264 |
| 5,344,655 | 9/1994 | Sakai et al. | 424/443 |

FOREIGN PATENT DOCUMENTS

| | | |
|---|---|---|
| 97036 | 12/1983 | European Pat. Off. . |
| 3-275619 | 12/1991 | Japan . |
| 1288641 | 9/1972 | United Kingdom . |
| 2119709 | 11/1983 | United Kingdom . |

OTHER PUBLICATIONS

"Candida Tropicalis Vulvovaginitis", Horowitz eta l., Obstetrics & Gynecology, vol. 66, No. 2, Aug. 1985.
"Butoconzaole—Pharmacologic Considerations Chemistry and Microbiology", Matthews, *Journal of Reproductive Medicine*, 1986; 31 (supp): pp. 655–657.
"Antifungal Therapy in the Management of Chronic Candidiasis", Horowitz, *Am J Obstet Gynecol*, 1988; 158:996.
"Mycotic Vulvovaginitis: A Broad Overview", Horowitz, *Am J Obstet Gynecol*, 1991; 165:1188–92.
"A New Vaginal Antifungal Agent—Butoconazole Nitrate", Jacobson et al., *Acta Obstet Gynecol Scand*, 1985; 64:317–321.
"Terazol® (Terconazole): A Technical Background".
PDR Lotrimin Lotrisone p. 1997 44 th ed 1990.
USPDI 1989 Clotrimazole pp. 2451, 851, 854.

*Primary Examiner*—Neil S. Levy
*Attorney, Agent, or Firm*—Mary Catherine Poland; Douglas C. Mohl; David K. Dabbiere

[57] ABSTRACT

The present invention relates to improved topical pharmaceutical compositions in the form of a wipe or towelette having improved aesthetics which are useful for imparting antimicrobial actives. In particular, it relates to topical moisturizing wipe compositions containing one or more antimicrobial active compounds. These compositions are also useful for providing relief from symptoms associated with, for example, vaginal yeast infections.

5 Claims, No Drawings

ANTIMICROBIAL WIPE COMPOSITIONS

This is a continuation of application Ser. No. 08/173,333, filed on Dec. 23, 1993, abandoned.

TECHNICAL FIELD

The present invention relates to improved topical pharmaceutical wipe compositions having improved aesthetics which are useful for imparting antimicrobial actives. In particular, it relates to wipe compositions impregnated with topical moisturizing compositions containing one or more antimicrobial active compounds. These compositions are also useful for providing relief from symptoms associated with, for example, vaginal yeast infections.

BACKGROUND OF THE INVENTION

Several environmental and pathologic conditions produce drying or desiccation of membranous tissue of the mammalian body. These conditions produce dry mouth (xerostomia), dry eye (sicca conditions) and dry vaginal, dry nasal or dry rectal mucosa, and/or dry skin that are aesthetically unpleasing and/or irritating to the individuals having such conditions.

One method for moisturization of dry tissue uses an oily substance as the principal ingredient in the form of creams, lotions, or salves that are applied to the affected tissue in an attempt to prevent further dehydration of the tissue. They act by placing a water-impermeable hydrophobic barrier over the treated tissue. Petrolatum, mineral oil, lanolin and isopropyl myristate are examples of hydrophobic materials so used. These preparations alone provide only symptomatic relief. In addition, they impart a greasy, sticky feel to the skin and stain clothing.

Another method for moisturization hydrophilic molecules which can attract water. Hydrophilic small molecules such as glycerin and glycerin/water mixtures, urea, and propylene glycol are known humectants said to be useful in moisturizing skin.

Several synthetic hydrophilic materials, which in the presence of water adhere to the skin and/or mucous membranes, have been used by themselves or in conjunction with one or more active or treating agents in various pathological conditions, but they have not been used in moisturizing compositions having a specific viscosity range, for dryness of epithelial cells such as those of the skin or mucosa. These hydrophilic materials are often referred to in the art as hydrogels.

Disorders in these mucosal areas can often lead to infections, such as a yeast infection. Yeast infections are among the most common to mankind. Microbes of the genus Candida are normal inhabitants of the bowel. These microbes are also found on the skin and in sputum of healthy individuals. *Candida albicans* is by far the most pathogenic member of the Candida family. Suitable treatments for such infections are well known. For example, U.S. Pat. No. 4,226,848 discloses a composition for adhering a pharmaceutical preparation to the mucosa of the oral or nasal cavities. An exemplary acrylic acid polymer disclosed therein is the lightly cross-linked acrylic acid-allyl sucrose copolymer available under the trademark CARBOPOL® 934 from B. F. Goodrich Chemical Co., which is said to form a high viscosity gel-like dispersion in water.

U.S. Pat. No. 4,548,990 discloses a controlled-release drug delivery composition whose cross-linked polymeric portion is prepared from monomers that include 50 to 99 percent of a water-insoluble monoolefinic monomer or mixture. The polymer is said to swell in ethanol and in water with a swelling ratio of 2:1 to 22:1.

Candida also causes vulvovaginitis, meningitis, pulmonary candidiasis, thrush, and endocarditis. It is most often associated, however with, the organism that is responsible for vaginal yeast infections in women. This condition occurs most frequently, and with greater severity, in areas where the climate is warm and moist. It often follows antibiotic therapy and is difficult to eradicate.

Conventional commercially-available treatments for vaginal yeast infections are creams which cause leakage and suffer serious negatives in terms of skinfeel (i.e. they often feel very tacky and greasy on the skin). They also have poor absorption and residue characteristics.

The present invention provides topical moisturizing wipes and the like which contain aqueous gel compositions which treat microbial infections which provide improvements in residue and skinfeel characteristics.

It is therefore an object of the present invention to provide improved wipe compositions which contain antimicrobial gel compositions which provide reduced tack and provide the user with an improved skinfeel.

SUMMARY OF THE INVENTION

The present invention relates to pharmaceutical compositions for moisturizing membranous tissue and treating infections comprising:

(a) a safe and effective amount of an antimicrobial;

(b) a moisturizing component; and (c) an pharmaceutically acceptable aqueous gel carrier wherein said composition has a viscosity of from about 40,000 cps to about 100,000 cps.

The present invention also relates to a method for treatment of dry membranous tissue and treating infections comprising administering a safe and effective amount of these topical compositions and to methods for the prophylactic treatment of infection by application of these compositions to healthy membranous tissue.

All levels and ratios are by weight of the total composition, unless otherwise indicated.

DETAILED DESCRIPTION OF THE INVENTION

The compositions of the present invention contain the essential components as well as various optional components as indicated below.

Humectants/Moisturizers.

The compositions of the instant invention comprise one or more water-soluble humectants/moisturizers. A variety of humectants/moisturizers can be employed and can be present at a level of from about 1% to about 10%, more preferably from about 2% to about 8% and most preferably from about 3% to about 5%. These materials include the $C_3$–$C_6$ diols and triols; urea; guanidine; glycolic acid and glycolate salts (e.g. ammonium and quaternary alkyl ammonium); lactic acid and lactate salts (e.g. ammonium and quaternary alkyl ammonium); polyhydroxy alcohols such as sorbitol, glycerin, hexanetriol, propylene glycol, hexylene glycol and the like; polyethylene glycol; sugars and starches; sugar and starch derivatives (e.g. alkoxylated glucose); D-panthenol; hyaluronic acid; lactamide monoethanolamine; acetamide monoethanolamine; and mixtures thereof.

Preferred humectants/moisturizers for use in the compositions of the present invention are the $C_3$–$C_6$ diols and triols. Especially preferred is the triol, glycerin.

Antimicrobial Agent

The antimicrobial agents useful in the present invention can be present at a level of from about 0.01% to about 4%, typically from about 0.1% to about 2%, and preferably from about 0.5% to about 1%. The level is selected to provide the desired level of antimicrobial activity and can be modified as desired.

Useful antimicrobial agents include those effective against *microsporum audouini*, *microsporum gypseum*, *microsporum gypseum-canis*, *epidermophyton floccosum*, *trichophyton mentagrophytes*, *trichophyton robrum*, *trichophyton tonsurans*, *cryptococcus neoformans* and the candida species, including *candida salbicans* and *candida tropicalis*.

In addition, the compounds of the present invention exhibit antimicrobial activity against human and animal pathogens, such as *staphylococcus aureus*, *streptococcus faecalis*, *corynebacterium acnes*, *erysipelothrix insidiosa*, *escherichia coli*, *proteus vulgaris*, *salmonella choleraesuis*, *pasteurella multocida*, *pseudomonas aeruginosa* and *trichomonas vaginalis*.

Many antimicrobial agents, known to those skilled in the art and disclosed in, e.g., U.S. Pat. Nos. 3,835,057 and 4,714,563, both incorporated herein by reference, may be used.

Suitable antimicrobial agents include: 2-hydroxy-4,2',4'-trichlorodiphenylether, (TCS); 2,6-dimethyl-4-hydroxychlorobenzene (PCMX); 3,4,4'-trichlorocarbanilide (TCC); 3-trifluoromethyl-4,4'-dichlorocarbanilide (TFC); 2,2'-dihydroxy-3,3',5,5',6,6'-hexachlorodiphenylmethane; 2,2'-dihydroxy-3,3',5,5'-tetrachlorodiphenylmethane; 2,2'-dihydroxy-3,3',dibromo-5,5'-dochlorodiphenylmethane; 2-hydroxy-4,4'-dichlorodiphenylether; 2-hydroxy-3,5',4-tribromodiphenylether; 1-hydroxy-4-methyl-6-(2,4,4-trimethylpentyl)-2(1H)-pyridinone (Octopirox); butoconazole, nystatin, terconazole, nitrofurantoin, phenazopyridine, acyclovir, clotrimazole, chlorohexidine, terconazole and miconazole. The most preferred antimicrobials of this group are butoconazole, nystatin, terconazole, nitrofurantoin, phenazopyridine, acyclovir, chlorohexidine, miconazole, and clotrimazole.

Also preferred for use herein are the 1-($\beta$3-aryl) ethylimidazole ethers and amines disclosed in U.S. Pat. No. 3,717,655 to Godefroi et al. issued Feb. 20, 1973 derivatives of substituted N-alkyl imidazoles disclosed in U.S. Pat. No. 4,078,071 to Walker, issued Mar. 7, 1978. Other preferred antimicrobials include the tin-containing polymers disclosed in U.S. Pat. No. 5,043,463 to Carraher Jr., et al., issued Aug. 27, 1991. All of these patents are incorporated by reference herein.

Pharmaceutical Carrier

The pharmaceutical compositions of the present invention may be made into a wide variety of product types having a pharmaceutically-acceptable aqueous-based gel-type carders. Such gel carriers contain a hydrophilic gelling agent at a level preferably from about 0.05% to about 1%, more preferably from about 0.1% to about 1%. The gelling agent preferably has a viscosity (1% aqueous solution, 20° C., Brookfield RVT) of at least about 4000 cps, more preferably at least about 10,000 cps, and most preferably at least about 50,000.

Suitable hydrophilic gelling agents can generally be described as water-soluble or colloidally water-soluble polymers, and include cellulose ethers (e.g. hydroxyethyl cellulose, methyl cellulose), hydroxypropyl guar gum and xanthan gum. Also useful are clays such as hectoritc (Veegum) and bentonite. Particularly preferred gelling agents useful in the present invention are polyacrylamides and substituted polyacrylamides, branched or unbranched. These polymers are non-ionic water-dispersible polymers which can be formed from a variety of monomers including acrylamide and methacrylamide which are unsubstituted or substituted with one or two alkyl groups (preferably $C_1$-$C_5$). Preferred acrylate amides and methacrylate amides in which the amide nitrogen is unsubstituted, or substituted with one or two $C_1$-$C_5$ alkyl groups (preferably: methyl, ethyl or propyl), for example, acrylamide, methacrylamide, N-methylacrylamide, N-methylmethacrylamide, N,N-dimethylmethacrylamide, N-isopropylacrylamide, N-isopropylmethacrylamide and N,N-dimethylacrylamide. These monomers are generally disclosed in U.S. Pat. No. 4,963,348 to Bolich, Jr. et al., issued Oct. 16, 1990, incorporated by reference herein in its entirety. These copolymers may optionally be formed using conventional neutral crosslinking agents such as dialkenyl compounds. The use of such crosslinking agents for cationic polymers is disclosed in U.S. Pat. No. 4,628,078 to Glover et al. issued Dec. 9, 1986 and U.S. Pat. No. 4,599,379 to Flesher et al. issued Jul. 8, 1986 both of which are incorporated by reference herein. These non-ionic copolymers have a molecular weight greater than about 1,000,000 preferably greater than about 1,500,000 and range up to about 30,000,000. Preferably these non-ionic polyacrylamides are predispersed in a water-immiscible solvent such as mineral oil and the like, containing a high HLB surfactant (HLB from about 7 to about 10) which helps to facilitate water dispersibility of the polyacrylamide. Most preferred for use herein is the non-ionic polymer under the CTFA designation: polyacrylamide and isoparrafin and laureth-7, available as Sepigel from Seppic Corporation.

In highly preferred embodiment, the compositions are substantially free of materials which are insoluble or not colloidally soluble in distilled water at 20° C. Such materials include many conventional emollient materials such as hydrocarbon oils and waxes, fatty alcohols, certain fatty alcohol ethers and sterols extracted from lanolin, beeswax derivatives, vegetable waxes, sterols and amides. The compositions can, however, contain low levels of insoluble ingredients added, for example for visual effect purposes, e.g., titianated mica.

These compositions may include additional co-solvents such as ethanol, isopropanol, butylene glycol, hexylene glycol, polyethylene glycol and polypropylene glycol.

The compositions of the invention have no need of additional surfactant materials which are conventionally added to cosmetic cream and lotion compositions in order to emulsify a water-insoluble oily phase.

The pharmaceutical compositions of the present invention typically include a pharmaceutically or cosmetically-acceptable organic solvent. The terms "pharmaceutically-acceptable organic solvent" and "cosmetically-acceptable organic solvent" refer to an organic solvent which also possesses acceptable safety (e.g. irritation and sensitization characteristics), as well as good aesthetic properties (e.g., does not feel greasy or tacky). The most typical example of such a solvent is water. Examples of other suitable organic solvents include: propylene glycol, polyethylene glycol (200-600), polypropylene glycol (425-2025), glycerol, 1,2,4-butanetriol, sorbitol esters, 1,2,6-hexanetriol, ethanol, isopropanol, butanediol, and mixtures thereof.

The compositions of the invention are formulated so as to have product viscosity in the range of from about 40,000 to about 100,000 cps, more preferably from about 40,000 to about 80,000 cps and especially from about 40,000 to about 60,000 cps (20° C., neat, Brookfield RVT). Preferably the compositions are visually translucent.

The compositions which are in aqueous form are also preferably substantially free of oil, i.e. contain less than about 1%, and preferably less than about 0.1% of materials which are insoluble or which are not colloidally-soluble in the aqueous gel matrix at 10° C. "Colloidally-soluble" herein refers to particles in the usual colloidal size range, typically from 1 to 1000 nm, especially from 1 to 500 nm. In highly preferred embodiment, the compositions are substantially free of materials which are insoluble or not colloidally soluble in distilled water at 20° C. Such materials include many conventional emollient materials such as hydrocarbon oils and waxes, fatty alcohols, certain fatty alcohol ethers and sterols extracted from lanolin, beeswax derivatives, vegetable waxes, sterols and amides. The compositions are also preferably substantially free of alcohol, i.e. contain less than about 5%, preferably less than about 0.3%, more preferably less than about 1% and most preferably less than about 0.5% alcohol. The compositions can, however, coma low levels of insoluble ingredients added, for example for visual effect purposes, e.g., titianated mica.

Optional Components

Emollients.

The compositions of the present invention preferably comprise at least one emollient. Useful emollients have a required HLB below about 10. Preferred emollients are volatile silicone oils, non-volatile emollients, and the highly branched hydrocarbons known as the Permethyl 99 through 108A series (available from Permethyl Corporation) and mixtures thereof. The compositions of the present invention more preferably comprise at least one volatile silicone oil which functions as a liquid emollient, or especially in a mixture of volatile silicone oils and non-volatile emollients. The term "volatile", as used herein, refers to those materials which have a measurable vapor pressure at ambient temperature.

Volatile silicone oils useful in the compositions of the present invention are preferably cyclic. The following formula illustrates cyclic volatile polydimethylsiloxanes useful in the compositions disclosed herein:

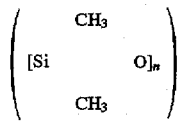

wherein n equals about 3 to about 7. Linear polydimethylsiloxanes contain from about 3 to about 9 silicon atoms per molecule and have the following general formula:

wherein n equals about 1 to about 7. Linear volatile silicone materials generally have viscosities of less than about 5 centistokes at 25° C. while cyclic materials typically have viscosities of less than about 10 centistokes. A description of various volatile silicone oils is found in Todd, et at., "Volatile Silicone Fluids for Cosmetics", *Cosmetics & Toiletries*, 91, pages 27–32 (1976), the disclosures of which are incorporated by reference herein in their entirety.

Examples of preferred volatile silicone oils useful herein include: Dow Corning 344, Dow Corning 345, and Dow Corning 200 (manufactured by Dow Corning Corp.); Silicone 7207 and Silicone 7158 (manufactured by the Union Carbide Corp.); SF 1202 (manufactured by General Electric); and SWS-03314 (manufactured by SWS Silicones, Inc.).

The present compositions also preferably contain one or more non-volatile emollients. Such materials include fatty acid and fatty alcohol esters, hydrocarbons, non-volatile silicone oils, and mixtures thereof. Emollients among those useful herein are described in 1 *Cosmetics, Science and Technology.* 27–104 (M. Balsam and E. Sagatin, Ed.; 1972), and U.S. Pat. No. 4,202,879, to Shelton, issued May 13, 1980 (both incorporated by reference herein).

Non-volatile silicone oils useful as an emollient material include polyalkylsiloxanes and polyalklyarylsiloxanes. The essentially non-volatile polyalkyl siloxanes useful herein include, for example, polydimethyl siloxanes with viscosities of from about 5 to about 100,000 centistokes at 25° C. Among the preferred non-volatile emollients useful in the present compositions are the polydimethyl siloxanes having viscosities from about 10 to about 400 centistokes at 25° C. Such polyalkyl siloxanes include the Vicasil series (sold by General Electric Company) and the Dow Corning 200 series (sold by Dow Corning Corporation). Polyalkylaryl siloxanes include poly methylphenyl siloxanes having viscosities of from about 15 to about 65 centistokes at 25° C. These are available, for example, as SF 1075 methylphenyl fluid (sold by General Electric Company) and 556 Cosmetic Grade Fluid (sold by Dow Corning Corporation).

Non-polar fatty acid and fatty alcohol esters useful herein as an emollient material include, for example, ethyl hexyl palmitate, isodecyl neopentanoate, octadodecyl benzoate, diethyl hexyl maleate and PPG-2 myristyl ether propionate. Hydrocarbons such as isohexadecane (e.g., Permethyl 101A supplied by Presperse), petrolatum and USP light (e.g. Klearol®) or heavy (e.g. Kaydol®) mineral oils are also useful as emollients. Emollients useful in the instant invention are further described in U.S. Pat. No. 4,919,934, to Deckner et at., issued Apr. 24 1990, which is incorporated herein by reference in its entirety.

The emollients typically comprise in total from about 1% to about 50%, preferably from about 1% to about 25%, and more preferably from about 1% to about 10% by weight of the compositions of the present invention.

Thickening Agents.

The composition may also comprise from about 0.1% to about 2% of a thickening agent. Examples of suitable thickening agents include: cellulose derivatives (e.g., methyl cellulose and hydroxy propylmethyl cellulose), synthetic high molecular weight polymers (e.g., carboxyvinyl polymer and polyvinyl alcohol), plant hydrocolloids (e.g., karaya gum and tragacanth gum), clay thickeners (e.g., colloidal magnesium aluminum silicate and bentonite), and carboxyvinyl polymers are described in detail in U.S. Pat. No. 2,798,053, Brown, issued Jul. 2, 1975, incorporated herein by reference). A more complete disclosure of thickening agent useful herein can be found in Segarin, *Cosmetics, Science and Technology,* 2nd Edition, Vol. 1, pp. 72–73 (1972), incorporated herein by reference.

Additional Pharmaceutical Actives.

Optional pharmaceutical actives useful in the present invention include any chemical material or compound suitable for topical administration; however, such drugs should be included so as not to interfere with the stability of the composition. These actives are present at a level from about 0.1% to about 20%. Such substances include, but are not limited to vitamins, analgesics, anti-inflammatory agents, antipuritics, antipyretics, anesthetic agents, and mixtures thereof.

A safe and effective amount of an anti-inflammatory agent may be added to the compositions of the present invention, preferably from about 0.1% to about 10%, more preferably from about 0.5% to about 5%, of the composition. The exact amount of anti-inflammatory agent to be used in the compositions will depend on the particular anti-inflammatory agent utilized since such agents vary widely in potency.

Steroidal anti-inflammatory agents, including but not limited to, corticosteroids such as hydrocortisone, hydroxyltriamcinolone, alpha-methyl dexamethasone, dexamethasone-phosphate, beclomethasone dipropionate, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylester, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone acetonide, medrysone, amcinafel, amcinafide, betamethasone and the balance of its esters, chloroprednisone, chlorprednisone acetate, clocortelone, clescinolone, dichlorisone, difluprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof may be used. The preferred steroidal anti-inflammatory for use in the present invention is hydrocortisone.

A second class of anti-inflammatory agents which is useful in the compositions of the present invention includes the nonsteroidal anti-inflammatory agents. The variety of compounds encompassed by this group are well-known to those skilled in the art. For detailed disclosure of the chemical structure, synthesis, side effects, etc., of nonsteroidal anti-inflammatory agents, reference may be had to standard texts, including *Anti-inflammatory and Anti-Rheumatic Drugs*, K. D. Rainsford, Vol. I–III, CRC Press, Boca Raton, (1985), and *Anti-inflammatory Agents, Chemistry and Pharmacology*, 1, R. A. Scherrer, et al., Academic Press, New York (1974).

Specific non-steroidal anti-inflammatory agents useful in the composition of the present invention include, but are not limited to:

1) the oxicams, such as piroxicam, isoxicam, tenoxicam, sudoxicam, and CP-14,304;

2) the salicylates, such as aspirin, disalcid, benorylate, trilisate, safapryn, solprin, diflunisal, and fendosal;

3) the acetic acid derivatives, such as didofenac, fenclofenac, indomethacin, sulindac, tolmetin, isoxepac, furofenac, tiopinae, zidometacin, acematacin, fentiazac, zomepiract, clidanac, oxepinac, and felbinac;

4) the fenamates, such as mefenamic, meclofenamic, flufenamic, niflumic, and tolfenamic acids;

5) the propionic acid derivatives, such as ibuprofen, naproxen, benoxaprofen, flurbiprofen, ketoprofen, fenoprofen, fenbufen, indoprofen, pirprofen, carprofen, oxaprozin, pranoprofen, miroprofen, tioxaprofen, suprofen, alminoprofen, and tiaprofenic; and 6) the pyrazoles, such as phenybutazone, oxyphenbutazone, feprazone, azapropazone, and trimethazone.

Mixtures of these non-steroidal anti-inflammatory agents may also be employed, as well as the pharmaceutically-acceptable salts and esters of these agents. For example, etofenamate, a flufenamic add derivative, is particularly useful for topical application. Of the nonsteroidal anti-inflammatory agents, ibuprofen, naproxen, flufenamic, acid, mefenamic acid, meclofenamic acid, piroxicam and felbinac are preferred; ibuprofen, naproxen, and flufenamic acid are most preferred.

Another class of anti-inflammatory agents which are useful in the present invention are the anti-inflammatory agents disclosed in U.S. Pat. No. 4,708,966, Loomans et al., issued Nov. 24, 1987. This patent discloses a class of nonsteroidal anti-inflammatory compounds which comprise specifically substituted phenyl compounds, especially substituted 2,6-di-tert-butyl phenol derivatives. For example, compounds selected from 4-(4'-pentyn-3'-one)-2,6-di-t-butylphenol; 4-(5'-hexynoyl)-2,6-di-t-butylphenol; 4-((S)-(−)- 3'-methyl-5'-hexynoyl)-2,6-di-t-butylphenol; 4-((R)-(+)-3'-methyl-5'-hexynoyl)-2,6-di-t-butylphenol; and 4-(3',3'-dimethoxypropionyl)-2,6-di-t-butylphenol are useful in the present invention.

Yet another class of anti-inflammatory agents which are useful in the present invention are those disclosed in U.S. Pat. No. 4,912,248, Mueller, issued Mar. 27, 1990. This patent discloses compounds and diastereomeric mixtures of specific 2-naphthyl- containing ester compounds, especially naproxen ester and naproxol ester compounds, having two or more chiral centers.

Finally, so-called "natural" anti-inflammatory agents are useful in the present invention. For example, candelilla wax, alpha bisabolol, aloe vera, Manjistha (extracted from plants in the genus Rubia, particularly *Rubia Cordifolia*), and Guggal (extracted from plants in the genus Commiphora, particularly *Commiphora Mukul*), may be used.

Useful anesthetic or antipruritic drugs are selected from the group consisting of lidocaine, lidocaine hydrochloride, bupivacaine hydrochloride, chlorprocaine hydrochloride, dibucaine hydrochloride, etidocaine hydrochloride, mepivacaine hydrochloride, tetracaine, tetracaine hydrochloride, dyclonine hydrochloride and hexylcaine hydrochloride, benzocaine, benzyl alcohol, butamben picrate, camphor, camphorated metacresol, dibucaine, dibucaine hydrochloride, dimethisoquin hydrochloride, diphenhydramine hydrochloride, juniper tar, menthol, phenol, phenolate sodium, pramoxine hydrochloride, resorcinol and mixtures thereof.

Other Optional Components.

A variety of additional ingredients may be added to the emulsion compositions of the present invention. These additional ingredients include various polymers for aiding the film-forming properties and substantivity of the formulation, preservatives for maintaining the antimicrobial integrity of the compositions, antioxidants, and agents suitable for aesthetic purposes such as fragrances, pigments, and colorings.

The compositions can also contain low levels of insoluble ingredients added, for example for visual effect purposes, e.g. thermochromic liquid crystalline materials such as the microencapsulated cholesteryl esters and chiral nematic (nonsterol) based chemicals such as the (2-methylbutyl) phenyl 4-alkyl(oxy)benzoates available from Hallcrest, Glenview, Ill. 60025, U.S.A.

Also preferred for use herein is a bioadhesive which will adhere the microbial agent of the present invention to the skin tissues treated herein. Useful bioadhesives are described in U.S. Pat. No. 4,983,392 to Robinson et al., incorporated by reference herein.

The pH of the compositions is preferably from about 3 to about 8, more preferably from about 3 to about 7.

The amount of active components and frequency of treatment will vary widely depending upon the individual.

STRUCTURAL FIBERS

The present invention contains woven or nonwoven fabrics derived from "oriented" or carded fibrous webs composed of textile-length fibers, the major proportion of which are oriented predominantly in one direction. These compositions can be in the form of, for example, wipes or towelettes (including baby wipes and the like) or also incorporated into feminine hygiene products such as sanitary napkins and the like.

Preferred for use herein are nonwoven fabrics. The convention base starting material for the majority of these nonwoven fabrics is usually a fibrous web comprising any of the common textile-length fibers, or mixtures thereof, the fibers varying in average length from approximately ½ inch to about 3 inches, preferably 1½ to 2 inches. Exemplary of such fibers are the natural fibers such as cotton and wool and the synthetic or man-made cellulosic fibers, notably rayon or regenerated cellulose, such as those supplied by BASF.

Other textile-length fibers of a synthetic or man-made origin may be used in various proportions to replace either partially or perhaps even entirely the previously-named fibers. Such other fibers include: polyamide fibers such as nylon 6, nylon 66, nylon 610, etc.; polyester fibers such as "Dacron", "Fortrel" and "Kodel"; acrylic fibers such as "Acrilan", "Orlon" and "Creslan"; modacrylic fibers derived from polyethylene and polypropylene; cellulose ester fibers such as "Arnel" and "Acele"; polyvinyl alcohol fibers, etc.

These textile-length fibers may be replaced either partially or entirely by fibers having an average length of less than about one-half inch and down to about one-quarter inch. These fibers, or mixtures, thereof, are customarily processed through any suitable textile machinery (e.g., a conventional cotton card, a "Rando-Webber" a paper-making machine, or other fibrous web producing apparatus) to form a web or sheet of loosely associated fibers, weighing from about 100 grains to about 2,000 grains per square yard or even higher.

If desired, even shorter fibers, such as wood pulp fibers or cotton linters, may be used in varying proportions, even up to 100%, where such shorter length fibers can be handled and processed by available apparatus. Such shorter fibers have lengths less than ¼ inch.

The resulting fibrous web or sheet, regardless of its method of production, is then subjected to at least one of several types of bonding operations to anchor the individual fibers together to form a self-sustaining web incorporating the resins described infra. One method is to impregnate the fibrous web over its entire surface area with the resins of the present invention. Such over-all impregnation produces a nonwoven fabric of good longitudinal and cross strength, acceptable durability and solvent resistable and satisfactory abrasion resistance.

Methods of making nonwoven cloths are not a part of this invention and, being well known in the art, are not described in detail herein. Generally, however, such cloths are made by air- or water-laying processes in which the fibers or filaments are first cut to desired lengths from long strands, passed into a water or air stream, and then deposited onto a screen through which the fiber-laden air or water is passed. The deposited fibers or filaments are then adhesively bonded together, using the resins of the present invention, dried, cured, and otherwise treated as desired to form the nonwoven cloth.

Thermocarded nonwoven cloths (whether or not resin containing) are made of polyesters, polyamides, or other thermoplastic fibers which can be spand bonded, i.e., the fibers are spun out onto a flat surface and bonded (melted) together by heat or chemical reactions, thereby not utilizing a resin. Such non-weaving can be bonded together utilizing the resins of the principal invention to form dual-laminated pads.

The preferred nonwoven cloth substrates used in the invention herein are generally adhesively bonded fibers or filamentous products having a web or carded fiber structure (when the fiber strength is suitable to allow carding) or comprising fibrous mats in which the fibers or filaments are distributed haphazardly or in random array (i.e., an array of fibers in a carded web where partial orientation of the fibers is frequently present, as well as a completely haphazard distributional orientation), or substantially aligned. The fibers or filaments can be natural (e.g., wool, silk, jute, hemp, cotton, linen, sisal, or ramie) or synthetic (e.g., rayon, cellulose ester, polyvinyl derivatives, polyolethins, polyamides, or polyesters) as have been described hereinabove. These nonwoven materials are generally described in Riedel "Nonwoven Bonding Methods and Materials", *Nonwoven World*, (1987).

Also useful herein are dual texture laminated nonwovens with slightly more coarse (or highly textured) nonwoven laminated to a smoother nonwoven. The more coarse nonwoven preferably has a denier of above about 5, preferably above about 8 and a loft of above about 60 mills, preferably above about 70 mills and the smooth side has a denier of from about 1 to about 4, preferably from about 1 to about 3, and a loft from about 10 to about 60, preferably from about 10 to about 50. Also highly preferred for use herein are air-laid cellulose based nonwovens with a loft of from about 50 to about 150. The loft of these materials can be measured by an Ames 482 guage micrometer using a 2 inch foot and a 5 pound weight. Most preferred compositions herein are dual textured pads comprising a high loft carded nonwoven fabric resin-bonded to an air-laid nonwoven. Such pads are made by conventional techniques such as print laying the resin onto one of the substrate materials and nipping or by saturation of the materials and nipping.

The absorbent properties preferred herein are particularly easy to obtain with nonwoven cloths and are provided merely by building up the thickness of the cloth, i.e., by superimposing a plurality of carded webs or mats to a thickness adequate to obtain the necessary absorbent properties, or by allowing a sufficient thickness of the fibers to deposit on the screen. Any denier of the fiber (generally up to about 15 denier) can be used, inasmuch as it is the free space between each fiber that makes the thickness of the cloth directly related to the absorbent capacity of the cloth. Thus, any thickness necessary to obtain the required absorbent capacity can be used.

The fabric material is then saturated with the antimicrobial moisturizing composition using conventional techniques.

For treatment, the wipe composition is applied to the mucosal skin via topical application of a safe and effective amount of the composition to treat an existing fungal, microbial or protozoal growth. Preferably, the wipe compositions of the present invention are used to treat vaginal yeast infections. The amount of actives delivered from the wipe and frequency of topical application to the skin can vary widely, depending upon personal needs, but it is suggested as an example that topical application range from about once per day to about four times daily, preferably from about twice per day to about three times daily. The amount of antifungal agents applied is generally from about 1 mg to about 2 mg per cm2 skin. The wipe compositions of the present invention can also be used prophylactically by their administrsation to healthy membranous tissues to guard from or prevent infections using the dosing regimen described above.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

Ingredients are identified by chemical or CTFA name.

Example I

An antimicrobial wipe composition is made by combining the following components using conventional mixing technology.

| Ingredient | (% W/W) |
| --- | --- |
| Polyacrylamide and $C_{13-14}$ Isoparaffin and Laureth-7[1] | 4.0 |
| Clotrimazole | 2.0 |
| PPG-14 Butylether | 8.0 |
| Water, Purified | q.s. |

[1]Available as Sepigel from Seppic Corporation.

| Pad Composition | Weight % |
| --- | --- |
| Polypropylene[1] | 75.0 |
| Rayon[2] | 25.0 |

[1]Obtained from Hercules Corporation
[2]Obtained from BASF Wyandotte.

Water is added to a suitable size container. While mixing at a moderate speed (300 rpm), the Polyacrylamide and $C_{13-14}$ Isoparaffin and Laureth-7 is added to the water. Separately, the PPG-14 Butyl ether is placed in a container and covered. Using a Lightnin' Mixer with a 3 blade paddle prop, the clotrimazole is added to the PPG-14 Butyl ether and mixed at a low speed (100 rpm) until the clotrimazole is dissolved. The PPG-14 Butyl ether is slowly added to the water phase to form a gel. The resulting gel is mixed at moderate speed until uniform. The pad composition is then saturated in this aqueous gel composition and cut into 10 cm by 10 cm squares.

The compositions display improved skinfeel and residue characteristics together with excellent moisturizing and emolliency characteristics.

Example II

An antimicrobial composition is made by combining the following ingredients utilizing conventional mixing techniques as described above in Example I.

| Ingredient | (% W/W) |
| --- | --- |
| Polyacrylamide and $C_{13-14}$ Isoparaffin and Laureth-7 | 4.0 |
| benzocaine | 3.0 |
| clotrimazole | 2.0 |
| PPG-14 butyl ether | 8.0 |
| Water, Purified | q.s. |

| Pad Composition | Weight % |
| --- | --- |
| Polypropylene[1] | 75.0 |
| Rayon[2] | 25.0 |

[1]Obtained from Hercules Corporation
[2]Obtained from BASF Wyandotte.

Example III

An antimicrobial composition is made by combining the following ingredients utilizing conventional mixing techniques as described above in Example I.

| Ingredient | (% W/W) |
| --- | --- |
| PPG-14 butyl ether | 8.000 |
| Polyacrylamide and $C_{13-14}$ Isoparaffin and Laureth-7 | 4.000 |
| clotrimazole | 2.000 |
| Ibuprofen | 5.000 |
| Glycerin | 1.000 |
| Aloe Vera Gel | 0.500 |
| Disodium EDTA | 0.005 |
| Water, Purified | q.s. |

| Pad Composition | Weight % |
| --- | --- |
| Polypropylene[1] | 75.0 |
| Rayon[2] | 25.0 |

[1]Obtained from Hercules Corporation
[2]Obtained from BASF Wyandotte.

What is claimed is:

1. A pharmaceutical composition for moisturizing membranous tissue and treating infections comprising:
    (a) an antimicrobial moisturizing composition comprising:
        (i) from about 0.01% to about 4% of clotrimazole;
        (ii) from about 1% to about 10% of a moisturizing component selected from the group consisting of $C_3$–$C_6$ diols and triols; and
        (iii) a pharmaceutically-acceptable aqueous gel carrier consisting essentially of from about 0.05% to about 1% of a water-soluble, nonionic polyacrylamide gelling agent comprising monomers selected from the group consisting of acrylamides and methacrylamides wherein said composition has a viscosity of from about 40,000 to about 100,000 cps (20° C., neat, Brookfield RVT); and
    (b) one or more layers of a polypropylene fabric material wherein at least one layer of the polypropylene fabric material has a denier of above about 8 and a loft of above about 70 mills and wherein at least one other layer of the polypropylene fabric material has a denier of from about 1 to about 2 and a loft of from about 10 to about 50 mills.

2. A pharmaceutical composition according to claim 1 wherein said polyacrylamide comprises monomers selected from acrylamide and methacrylamide which are unsubstituted or substituted with at least one alkyl groups having from about 1 to about 5 carbon atoms.

3. A pharmaceutical composition according to claim 2 wherein said wherein said composition has a viscosity of from about 40,000 to about 80,000 cps.

4. A pharmaceutical composition according to claim 1 wherein said composition further comprises an additional pharmaceutical active.

5. A pharmaceutical composition according to claim 4 wherein said additional pharmaceutical active is selected from the group consisting of vitamins, analgesics, anti-inflammatory agents, antipuritics, antipyretics, anesthetic agents, and mixtures thereof.

* * * * *

UNITED STATES PATENT AND TRADEMARK OFFICE
CERTIFICATE OF CORRECTION

PATENT NO. : 5,686,088
DATED : November 11, 1997
INVENTOR(S) : SEKHAR MITRA
GEORGE ENDEL DECKNER It is certified that error appears in the above-identified patent and that said Letters Patent is hereby corrected as shown below:

Column 3, line 41, "β3-aryl" should be --β-aryl--.

Column 3, line 54, "carders" should be --carriers--.

Column 5, line 22, "coma" should be --contain--.

Column 7, line 52, "didofenac" should be --diclofenac--.

Column 7, line 54, "tiopinae" should be --tiopinac--.

Column 8, line 2, "add" should be --acid--.

Column 8, line 4, delete the comma after the word "flufenamic".

Column 11, line 22 (Example I), the % W/W 4.0 should be moved one line down, across from the ingredient Isoparaffin and Laureth-7

Column 11, line 61 (Example II), the % W/W 4.0 should be moved one line down, across from the ingredient Isoparaffin and Laureth-7

Signed and Sealed this

Twenty-ninth Day of September, 1998

Attest:

BRUCE LEHMAN

Attesting Officer

Commissioner of Patents and Trademarks